US008956650B2

(12) United States Patent
Ohta et al.

(10) Patent No.: US 8,956,650 B2
(45) Date of Patent: Feb. 17, 2015

(54) INTRABUCCALLY RAPIDLY DISINTEGRATING TABLET AND A PRODUCTION METHOD OF THE TABLETS

(71) Applicant: Kyowa Hakko Kirin Co., Ltd, Tokyo (JP)

(72) Inventors: Motohiro Ohta, Shizuoka (JP); Eiji Hayakawa, Shizuoka (JP); Kunio Ito, Shizuoka (JP); Sanji Tokuno, Tokyo (JP); Kiyoshi Morimoto, Shizuoka (JP); Yasushi Watanabe, Shizuoka (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 0 days.

(21) Appl. No.: 13/744,179

(22) Filed: Jan. 17, 2013

(65) Prior Publication Data

US 2013/0281546 A1    Oct. 24, 2013

Related U.S. Application Data

(60) Continuation of application No. 13/282,271, filed on Oct. 26, 2011, now Pat. No. 8,357,396, which is a division of application No. 10/356,641, filed on Jun. 20, 2003, now Pat. No. 8,071,128, which is a continuation-in-part of application No. 09/147,374, filed as application No. PCT/JP97/02032 on Jun. 12, 1997, now abandoned.

(51) Int. Cl.
 *A61K 9/20* (2006.01)

(52) U.S. Cl.
 USPC ............ 424/464; 424/470; 424/489; 424/494

(58) Field of Classification Search
 None
 See application file for complete search history.

(56) References Cited

U.S. PATENT DOCUMENTS

| | | |
|---|---|---|
| 3,184,386 A | 5/1965 | Stephenson |
| 3,558,768 A | 1/1971 | Klippel |
| 3,885,026 A | 5/1975 | Heinemann et al. |
| 4,078,051 A | 3/1978 | Pomot et al. |
| 4,138,475 A | 2/1979 | McAinsh et al. |
| 4,248,857 A | 2/1981 | DeNeale et al. |
| 4,292,017 A | 9/1981 | Doepel |
| 4,305,502 A | 12/1981 | Gregory et al. |
| 4,369,172 A | 1/1983 | Schor et al. |
| 4,371,516 A | 2/1983 | Gregory et al. |
| 4,389,330 A | 6/1983 | Tice et al. |
| 4,389,393 A | 6/1983 | Schor et al. |
| 4,542,042 A | 9/1985 | Samejima et al. |
| 4,556,678 A | 12/1985 | Hsiao |
| 4,587,118 A | 5/1986 | Hsiao |
| 4,628,098 A | 12/1986 | Nohara et al. |
| 4,661,647 A | 4/1987 | Serpelloni et al. |
| 4,670,459 A | 6/1987 | Sjoerdsma |
| 4,689,333 A | 8/1987 | Nohara et al. |
| 4,698,101 A | 10/1987 | Koivurinta |
| 4,708,867 A | 11/1987 | Hsiao |
| 4,713,248 A | 12/1987 | Kjornaes et al. |
| 4,716,041 A | 12/1987 | Kjornaes et al. |
| 4,728,512 A | 3/1988 | Mehta et al. |
| 4,743,248 A | 5/1988 | Bartoo et al. |
| 4,752,470 A | 6/1988 | Mehta |
| 4,757,090 A | 7/1988 | Salpekar et al. |
| 4,760,093 A | 7/1988 | Blank et al. |
| 4,780,318 A | 10/1988 | Appelgren et al. |
| 4,786,508 A | 11/1988 | Ghebre-Sellassie et al. |
| 4,800,087 A | 1/1989 | Mehta |
| 4,803,213 A | 2/1989 | Iida et al. |
| 4,824,675 A | 4/1989 | Wong et al. |
| 4,832,880 A | 5/1989 | Staniforth |
| 4,840,799 A | 6/1989 | Appelgren et al. |
| 4,851,226 A | 7/1989 | Julian et al. |
| 4,851,229 A | 7/1989 | Magruder et al. |
| 4,863,742 A | 9/1989 | Panoz et al. |
| 4,871,549 A | 10/1989 | Ueda et al. |
| 4,874,613 A | 10/1989 | Hsiao |
| 4,886,669 A | 12/1989 | Ventouras |
| 4,892,741 A | 1/1990 | Ohm et al. |
| 4,894,240 A | 1/1990 | Geoghegan et al. |
| 4,898,737 A | 2/1990 | Panoz et al. |
| 4,915,949 A | 4/1990 | Wong et al. |
| 4,938,968 A | 7/1990 | Mehta |

(Continued)

FOREIGN PATENT DOCUMENTS

| | | |
|---|---|---|
| EP | 0052492 B1 | 2/1984 |
| EP | 0166440 A2 | 1/1986 |

(Continued)

OTHER PUBLICATIONS

European Search Report, 6 pages, EP appl. No. 13167223.0 (mailed Aug. 21, 2013).

(Continued)

*Primary Examiner* — Hasan Ahmed
(74) *Attorney, Agent, or Firm* — Cooley LLP

(57) ABSTRACT

An intrabuccally rapidly disintegrating tablet which is manufactured by a simple method, has an enough practical hardness and is rapidly disintegrated in the buccal cavity and its production method. The intrabuccally rapidly disintegrating tablet is produced by growing a powder material into a granulated material with a fixed particle diameter, the powder material including a sugar alcohol or a saccharide as main ingredient, each of which is first particle having an average particle diameter of not more than 30 µm, by mixing thus obtained granulated material with an active ingredient and a disintegrant, and by compressing the mixture into a predetermined shape.

12 Claims, No Drawings

(56) References Cited

U.S. PATENT DOCUMENTS

| | | |
|---|---|---|
| 4,946,684 A | 8/1990 | Blank et al. |
| 4,957,745 A | 9/1990 | Jonsson et al. |
| 4,968,508 A | 11/1990 | Oren et al. |
| 4,971,805 A | 11/1990 | Kitanishi et al. |
| 4,983,401 A | 1/1991 | Eichel et al. |
| 5,006,345 A | 4/1991 | Lang |
| 5,011,692 A | 4/1991 | Fujioka et al. |
| 5,013,557 A | 5/1991 | Tai |
| 5,013,743 A | 5/1991 | Iwahi et al. |
| 5,017,122 A | 5/1991 | Staniforth |
| 5,017,381 A | 5/1991 | Maruyama et al. |
| 5,026,559 A | 6/1991 | Eichel et al. |
| 5,026,560 A | 6/1991 | Makino et al. |
| 5,039,540 A | 8/1991 | Ecanow |
| 5,045,321 A | 9/1991 | Makino et al. |
| 5,073,374 A | 12/1991 | McCarty |
| 5,075,114 A | 12/1991 | Roche |
| 5,079,018 A | 1/1992 | Ecanow |
| 5,082,669 A | 1/1992 | Shirai et al. |
| 5,084,278 A | 1/1992 | Mehta |
| 5,093,132 A | 3/1992 | Makino et al. |
| 5,104,648 A | 4/1992 | Denton et al. |
| 5,112,616 A | 5/1992 | McCarty |
| 5,133,974 A | 7/1992 | Paradissis et al. |
| 5,137,733 A | 8/1992 | Noda et al. |
| 5,149,542 A | 9/1992 | Valducci |
| 5,160,680 A | 11/1992 | Serpelloni et al. |
| 5,169,640 A | 12/1992 | France et al. |
| 5,178,878 A | 1/1993 | Wehling et al. |
| 5,204,121 A | 4/1993 | Bucheler et al. |
| 5,211,957 A | 5/1993 | Hagemann et al. |
| 5,213,808 A | 5/1993 | Bar-Shalom et al. |
| 5,229,131 A | 7/1993 | Amidon et al. |
| 5,229,135 A | 7/1993 | Philippon et al. |
| 5,238,686 A | 8/1993 | Eichel et al. |
| 5,252,337 A | 10/1993 | Powell |
| 5,256,699 A | 10/1993 | Murphy et al. |
| 5,260,068 A | 11/1993 | Chen |
| 5,260,069 A | 11/1993 | Chen |
| 5,275,827 A | 1/1994 | Spinelli et al. |
| 5,376,384 A | 12/1994 | Eichel et al. |
| 5,409,711 A | 4/1995 | Mapelli et al. |
| 5,433,959 A | 7/1995 | Makino et al. |
| 5,439,689 A | 8/1995 | Hendrickson et al. |
| 5,445,829 A | 8/1995 | Paradissis et al. |
| 5,464,632 A | 11/1995 | Cousin et al. |
| 5,466,464 A | 11/1995 | Masaki et al. |
| 5,470,584 A | 11/1995 | Hendrickson et al. |
| 5,472,708 A | 12/1995 | Chen |
| 5,478,573 A | 12/1995 | Eichel et al. |
| 5,489,436 A | 2/1996 | Hoy et al. |
| 5,501,861 A | 3/1996 | Makino et al. |
| 5,506,345 A | 4/1996 | Riley et al. |
| 5,508,040 A | 4/1996 | Chen |
| 5,529,790 A | 6/1996 | Eichel et al. |
| 5,536,507 A | 7/1996 | Abramowitz et al. |
| 5,567,441 A | 10/1996 | Chen |
| 5,576,014 A | 11/1996 | Mizumoto et al. |
| 5,609,883 A | 3/1997 | Valentine et al. |
| 5,612,059 A | 3/1997 | Cardinal et al. |
| 5,616,345 A | 4/1997 | Geoghegan et al. |
| 5,629,017 A | 5/1997 | Pozzi et al. |
| 5,639,475 A | 6/1997 | Bettman et al. |
| 5,643,630 A | 7/1997 | Hinzpeter et al. |
| 5,700,492 A | 12/1997 | Morimoto et al. |
| 5,720,974 A | 2/1998 | Makino et al. |
| 5,738,875 A | 4/1998 | Yarwood et al. |
| 5,747,068 A | 5/1998 | Mendizabal |
| 5,762,961 A | 6/1998 | Roser et al. |
| 5,788,987 A | 8/1998 | Busetti et al. |
| 5,807,577 A | 9/1998 | Ouali |
| 5,837,284 A | 11/1998 | Mehta et al. |
| 5,837,285 A | 11/1998 | Nakamichi et al. |
| 5,837,379 A | 11/1998 | Chen et al. |
| 5,840,329 A | 11/1998 | Bai |
| 5,876,759 A | 3/1999 | Gowan, Jr. |
| 5,891,474 A | 4/1999 | Busetti et al. |
| 5,900,252 A | 5/1999 | Calanchi et al. |
| 5,908,638 A | 6/1999 | Huber et al. |
| 5,968,554 A | 10/1999 | Beiman et al. |
| 6,024,981 A | 2/2000 | Khankari et al. |
| 6,024,982 A | 2/2000 | Oshlack et al. |
| 6,033,687 A | 3/2000 | Heinicke et al. |
| 6,039,979 A | 3/2000 | Gendrot et al. |
| 6,096,340 A | 8/2000 | Chen et al. |
| 6,099,859 A | 8/2000 | Cheng et al. |
| 6,099,863 A | 8/2000 | Gilis et al. |
| 6,099,865 A | 8/2000 | Augello et al. |
| 6,103,263 A | 8/2000 | Lee et al. |
| 6,106,861 A | 8/2000 | Chauveau et al. |
| 6,106,862 A | 8/2000 | Chen et al. |
| 6,123,962 A | 9/2000 | Makino et al. |
| 6,129,933 A | 10/2000 | Oshlack et al. |
| 6,136,345 A | 10/2000 | Grimmett et al. |
| 6,139,865 A | 10/2000 | Friend et al. |
| 6,139,877 A | 10/2000 | Debregeas et al. |
| 6,153,220 A | 11/2000 | Cumming et al. |
| 6,162,463 A | 12/2000 | Lippa |
| 6,169,105 B1 | 1/2001 | Wong et al. |
| 6,183,776 B1 | 2/2001 | Depui et al. |
| 6,190,692 B1 | 2/2001 | Busetti et al. |
| 6,221,392 B1 | 4/2001 | Khankari et al. |
| 6,221,402 B1 | 4/2001 | Itoh et al. |
| 6,228,398 B1 | 5/2001 | Devane et al. |
| 6,269,615 B1 | 8/2001 | Amborn et al. |
| 6,287,599 B1 | 9/2001 | Burnside et al. |
| 6,316,029 B1 | 11/2001 | Jain et al. |
| 6,328,994 B1 | 12/2001 | Shimizu et al. |
| 6,344,215 B1 | 2/2002 | Bettman et al. |
| 6,350,470 B1 | 2/2002 | Pather et al. |
| 6,350,471 B1 | 2/2002 | Seth |
| 6,365,182 B1 | 4/2002 | Khankari et al. |
| 6,368,625 B1 | 4/2002 | Siebert et al. |
| 6,368,628 B1 | 4/2002 | Seth |
| 6,372,253 B1 | 4/2002 | Daggy et al. |
| 6,391,335 B1 | 5/2002 | Pather et al. |
| 6,413,549 B2 | 7/2002 | Green et al. |
| 6,420,473 B1 | 7/2002 | Chittamuru et al. |
| 6,432,534 B1 | 8/2002 | Hayakawa et al. |
| 6,465,009 B1 | 10/2002 | Liu et al. |
| 6,465,010 B1 | 10/2002 | Lagoviyer et al. |
| 6,495,160 B2 | 12/2002 | Esposito et al. |
| 6,500,454 B1 | 12/2002 | Percel et al. |
| 6,500,457 B1 | 12/2002 | Midha et al. |
| 6,509,036 B2 | 1/2003 | Pather et al. |
| 6,531,152 B1 | 3/2003 | Lerner et al. |
| 6,551,617 B1 | 4/2003 | Corbo et al. |
| 6,579,535 B2 | 6/2003 | Valentine et al. |
| 6,596,311 B1 | 7/2003 | Dobetti |
| 6,602,521 B1 | 8/2003 | Ting et al. |
| 6,627,223 B2 | 9/2003 | Percel et al. |
| 6,641,838 B2 | 11/2003 | Pather et al. |
| 6,660,382 B2 | 12/2003 | Nouri et al. |
| 6,663,888 B2 | 12/2003 | Percel et al. |
| 6,663,893 B2 | 12/2003 | Corbo et al. |
| 6,740,341 B1 | 5/2004 | Holt et al. |
| 6,897,205 B2 | 5/2005 | Beckert et al. |
| 7,048,945 B2 | 5/2006 | Percel et al. |
| 8,071,128 B2 | 12/2011 | Ohta et al. |
| 8,357,396 B2 | 1/2013 | Ohta et al. |
| 8,367,111 B2 | 2/2013 | Venkatesh et al. |
| 2001/0007680 A1 | 7/2001 | Kolter et al. |
| 2001/0014340 A1 | 8/2001 | Ohta et al. |
| 2001/0046964 A1 | 11/2001 | Percel et al. |
| 2002/0054907 A1 | 5/2002 | Devane et al. |
| 2002/0077348 A1 | 6/2002 | Dean et al. |
| 2002/0142034 A1 | 10/2002 | Shimizu et al. |
| 2002/0187190 A1 | 12/2002 | Cade et al. |
| 2003/0064108 A1 | 4/2003 | Lukas et al. |
| 2003/0096791 A1 | 5/2003 | Gupte et al. |
| 2003/0113374 A1 | 6/2003 | Percel et al. |
| 2003/0134884 A1 | 7/2003 | Hazama et al. |
| 2003/0157173 A1 | 8/2003 | Percel et al. |
| 2003/0161888 A1 | 8/2003 | Fernandez et al. |

(56) References Cited

U.S. PATENT DOCUMENTS

| | | |
|---|---|---|
| 2003/0215500 A1 | 11/2003 | Ohta et al. |
| 2004/0047906 A1 | 3/2004 | Percel et al. |
| 2004/0121010 A1 | 6/2004 | Hirsh et al. |
| 2004/0122106 A1 | 6/2004 | Ohta et al. |
| 2004/0126427 A1 | 7/2004 | Venkatesh et al. |
| 2004/0131682 A1 | 7/2004 | Percel et al. |
| 2004/0137156 A1 | 7/2004 | Lee et al. |
| 2004/0242536 A1 | 12/2004 | Khoo et al. |
| 2005/0025824 A1 | 2/2005 | Percel et al. |
| 2005/0118268 A1 | 6/2005 | Percel et al. |
| 2005/0152974 A1 | 7/2005 | Boehm et al. |
| 2005/0232988 A1 | 10/2005 | Venkatesh et al. |
| 2005/0269722 A1 | 12/2005 | De Luigi Bruschi et al. |
| 2006/0057199 A1 | 3/2006 | Venkatesh et al. |
| 2006/0078614 A1 | 4/2006 | Venkatesh et al. |
| 2006/0105038 A1 | 5/2006 | Lai et al. |
| 2006/0105039 A1 | 5/2006 | Lai et al. |
| 2006/0121112 A1 | 6/2006 | Jenkins et al. |
| 2006/0233892 A1 | 10/2006 | Hendrix |
| 2006/0246134 A1 | 11/2006 | Venkatesh |
| 2006/0269607 A1 | 11/2006 | Percel et al. |
| 2007/0264358 A1 | 11/2007 | Wittlin |
| 2008/0069878 A1 | 3/2008 | Venkatesh et al. |
| 2009/0263480 A1 | 10/2009 | Lai et al. |
| 2011/0212171 A1 | 9/2011 | Venkatesh et al. |
| 2012/0128771 A1 | 5/2012 | Venkatesh |
| 2012/0135076 A1 | 5/2012 | Ohta et al. |

FOREIGN PATENT DOCUMENTS

| | | |
|---|---|---|
| EP | 0239361 A1 | 9/1987 |
| EP | 0349103 A1 | 1/1990 |
| EP | 0357369 A2 | 3/1990 |
| EP | 0391518 A2 | 10/1990 |
| EP | 0431877 A1 | 6/1991 |
| EP | 0453001 A1 | 10/1991 |
| EP | 0516345 A1 | 12/1992 |
| EP | 0538034 A1 | 4/1993 |
| EP | 0553777 A2 | 8/1993 |
| EP | 0650826 A1 | 5/1995 |
| EP | 0721777 A2 | 7/1996 |
| EP | 0815931 A1 | 1/1998 |
| EP | 0293347 A1 | 11/1998 |
| EP | 0294493 A1 | 12/1998 |
| EP | 0914818 A1 | 5/1999 |
| EP | 0914823 A1 | 5/1999 |
| EP | 1010423 A2 | 6/2000 |
| EP | 0582396 B1 | 1/2001 |
| EP | 1070497 A1 | 1/2001 |
| EP | 1072257 A1 | 1/2001 |
| EP | 1157690 A1 | 11/2001 |
| EP | 1156786 B1 | 3/2003 |
| EP | 1366759 A1 | 12/2003 |
| EP | 0914823 B1 | 12/2004 |
| EP | 2319498 A1 | 5/2011 |
| FR | 2679451 A1 | 1/1993 |
| FR | 2766089 A1 | 1/1999 |
| FR | 2778848 A1 | 11/1999 |
| GB | 2053787 A | 2/1981 |
| GB | 8824392.8 | 9/1989 |
| GB | 2224207 A | 5/1990 |
| JP | 41-11273 B | 6/1966 |
| JP | 49-69819 | 7/1974 |
| JP | 55-129224 A | 10/1980 |
| JP | 56-014098 A | 10/1981 |
| JP | 61-143316 A | 7/1986 |
| JP | 62-61916 A | 3/1987 |
| JP | 62-50445 B2 | 10/1987 |
| JP | 62-242616 A | 10/1987 |
| JP | 62-246513 A | 10/1987 |
| JP | 62-252723 A | 11/1987 |
| JP | 63-162619 A | 7/1988 |
| JP | 63-270624 A | 11/1988 |
| JP | 1-503385 A | 11/1989 |
| JP | 1-313420 A | 12/1989 |
| JP | 2-500747 A | 3/1990 |
| JP | 2-164824 A | 6/1990 |
| JP | 2-172918 A | 7/1990 |
| JP | 2-289512 A | 11/1990 |
| JP | 3-240724 A | 10/1991 |
| JP | 4-224517 A | 8/1992 |
| JP | 5-271054 A | 10/1993 |
| JP | 5-310558 A | 11/1993 |
| JP | 6-53658 B2 | 7/1994 |
| JP | 6-321790 A | 11/1994 |
| JP | 7-69889 A | 3/1995 |
| JP | 7-124231 A | 5/1995 |
| JP | 8-503482 A | 4/1996 |
| JP | 8-175978 A | 7/1996 |
| JP | 2002-154948 A | 5/2002 |
| JP | 2003-522141 A | 7/2003 |
| JP | 2005-508922 A | 4/2005 |
| NZ | 550608 A | 11/2005 |
| NZ | 554346 A | 5/2006 |
| WO | WO 88/08703 A1 | 11/1988 |
| WO | WO 88/08704 A2 | 11/1988 |
| WO | WO 92/10173 A1 | 6/1992 |
| WO | WO 93/00097 A1 | 1/1993 |
| WO | WO 93/12769 A1 | 7/1993 |
| WO | WO 93/13758 A1 | 7/1993 |
| WO | WO 93/15724 A1 | 8/1993 |
| WO | WO 94/08576 A1 | 4/1994 |
| WO | WO 94/12180 A1 | 6/1994 |
| WO | WO 97/41878 A1 | 11/1997 |
| WO | WO 97/47287 A1 | 12/1997 |
| WO | WO 99/04763 A1 | 2/1999 |
| WO | WO 00/25752 A1 | 5/2000 |
| WO | WO 00/33821 A1 | 6/2000 |
| WO | WO 00/42998 A1 | 7/2000 |
| WO | WO 00/51568 A1 | 9/2000 |
| WO | WO 00/59486 A2 | 10/2000 |
| WO | WO 01/13898 A2 | 3/2001 |
| WO | WO 01/72285 A1 | 10/2001 |
| WO | WO 01/80829 A2 | 11/2001 |
| WO | WO 02/13794 A1 | 2/2002 |
| WO | WO 02/43704 A1 | 6/2002 |
| WO | WO 02/057475 A1 | 7/2002 |
| WO | WO 02/085336 A1 | 10/2002 |
| WO | WO 03/013492 A1 | 2/2003 |
| WO | WO 03/039520 A1 | 3/2003 |
| WO | WO 03/026613 A1 | 4/2003 |
| WO | WO 03/041683 A2 | 5/2003 |
| WO | WO 03/043661 A1 | 5/2003 |
| WO | WO 03/047552 A2 | 6/2003 |
| WO | WO 2004/009058 A1 | 1/2004 |
| WO | WO 2004/022037 A1 | 3/2004 |
| WO | WO 2004/087111 A1 | 10/2004 |
| WO | WO 2005/097064 A2 | 10/2005 |
| WO | WO 2005/105049 A2 | 11/2005 |

OTHER PUBLICATIONS

"Low Substituted Hydroxypropylcellulose," Official Monographs for Part II, 2001, NRF, JP XIV, pp. 942-943.

Ahmed, Interview Summary, 2 pages, from U.S. Appl. No. 10/356,641 (mailed Jul. 29, 2008).

Ahmed, Interview Summary, 2 pages, from U.S. Appl. No. 10/356,641 (mailed May 15, 2009).

Ahmed, Interview Summary, 3 pages, from U.S. Appl. No. 10/356,641 (mailed Sep. 8, 2006).

Ahmed, Interview Summary, 4 pages, from U.S. Appl. No. 10/356,641 (mailed Aug. 2, 2006).

Ahmed, Office Action Summary, 10 pages, from U.S. Appl. No. 10/356,641 (mailed Jan. 10, 2006).

Ahmed, Office Action Summary, 13 pages, from U.S. Appl. No. 10/356,641 (mailed Apr. 14, 2008).

Ahmed, Office Action Summary, 15 pages, from U.S. Appl. No. 10/356,641 (mailed Jun. 15, 2007).

Ahmed, Office Action Summary, 20 pages, from U.S. Appl. No. 10/356,641 (mailed Aug. 19, 2009).

Ahmed, Office Action Summary, 24 pages, from U.S. Appl. No. 10/356,641 (mailed Jun. 10, 2010).

(56) References Cited

OTHER PUBLICATIONS

Ahmed, Office Action Summary, 44 pages, from U.S. Appl. No. 10/356,641 (mailed Dec. 11, 2008).
Ahmed, Office Action Summary, 7 pages, from U.S. Appl. No. 10/356,641 (mailed Jun. 13, 2006).
Ahmed, Office Action Summary, 7 pages, from U.S. Appl. No. 10/356,641 (mailed Nov. 30, 2006).
Ahmed, Office Action, 5 pages, U.S. Appl. No. 10/453,848, United States Patent and Trademark Office (Sep. 5, 2008).
Ahmed, Office Action, 6 pages, U.S. Appl. No. 10/453,848, United States Patent and Trademark Office (Apr. 15, 2009).
Ahmed, Office Action, 8 pages, U.S. Appl. No. 10/453,848, United States Patent and Trademark Office (Mar. 31, 2010).
Albrecht, International Search Report, 6 pages, from International Patent Appl. No. PCT/US02/31535, European Patent Office (Feb. 3, 2003).
Ahmed, Notice of Allowance, 8 pages, U.S. Appl. No. 13/282,271, United States Patent and Trademark Office (Sep. 24, 2012).
Anwar et al., "Chronotherapeutics for Cardiovascular Disease," Drugs 55(5):631-643 (1998).
Bauer et al., Pharmarzeutische Technologie, 5$^{th}$ Edition, 1997, Govi Verlag Frankfurt, pp. 164-166.
Berigan, "Atomoxetine Used Adjunctively With Selective Serotonin Reuptake Inhibitors to Treat Depression," Prim. Care. Companion J. Clin. Psychiatry 6(2):93-94 (2004).
Berko, Office Action, 6 pages, U.S. Appl. No. 10/453,848, United States Patent and Trademark Office (May 23, 2005).
Bodmeier et al., "Theophylline Tablets Coated with Aqueous Latexes Containing Dispersed Pore Formers," J. Pharm. Sci. 79(10):925-928 (1990).
Bredefeld, Office Action, 28 pages, U.S. Appl. No. 11/256,653, United States Patent and Trademark Office (Aug. 28, 2012).
Bussemer et al., "Pulsatile Drug-Delivery Systems," Crit. Rev. Ther. Drug. Carr. Sys. 18(5):433-458 (2001).
Chamdra, Examiner's first report on patent application 2005299490, 2 pages, Australia patent application No. 2005299490 (Mar. 12, 2010).
Citation in the Third Party Observation in the Opposition of European Patent No. EP 0914818 B1, Aug. 3, 2009.
Database WPI, Section Ch, Week 198748, Derwent Publications, Ltd., London, GB; AN 1987-338131, XP002156870.
Duncan, Examination Report, 2 pages, from New Zealand Patent Appl. No. 554346, New Zealand Patent Office, Wellington, New Zealand (mailed May 20, 2009).
Experimental data provided by Opponent I the Opposition of European Patent No. EP 0914818 B1, Jul. 28, 2009.
Fell, Letter to The Editor, J. Pharm. Pharmacol. 1968, vol. 20, pp. 657-658.
FMC Corporation Product Specification for Avicel PH, 2005.
Foreign non-patent publication from Japanese textbook, 1989, Hirokawa Publishing Co.
Foreign non-patent publication Sysmex No. FP30SCJ001 (2007).
Fubara, International Preliminary Examination Report, 3 pages, from International Patent Appl. No. PCT/US02/31535, European Patent Office (Jun. 19, 2003).
Fubara, Office Action, 4 pages, U.S. Appl. No. 10/334,052, United States Patent and Trademark Office (Dec. 1, 2003).
Gordon et al., "Effect of the Mode of Super Disintegrant Incoproration on Dissolution in Wet Granulated Tables," J. Pharm. Sci. 82:220-226 (1993).
Gorman et al., An Evaluation of Croscarmellose as a Tablet Disintegrant in Direct Compression Systems, Drug. Dev. Ind. Pharm. 1982; vol. 8, pp. 397-410.
Handbook (Binran) of Granule, vol. 1, Ohmsha Ltd., p. 434 & 438 (May 3, 1975).
Ishino et al., "Design and Preparation of Pulsatile Release Tablet as a New Oral Drug Delivery System," Chem. Pharm. Bull. 40(11):3036-3041 (1992).
Kaneto et al., 2000, Latest Pharmacy, Hirokawa Publishing Co., 1 Edition.

Kawashima, "Low-Substituted Hydroxypropylcellulose as a Sustained-Drug Release Matrix Base or Disintegrant Depending on Its Particle Size and Loading in Formulation," Pharm. Res. 1993, vol. 10(3), pp. 351-355.
Kornblum, "A New Tablet Disintegrating Agent," J. Pharm. Sci., Jan. 1973, vol. 62(1), pp. 43-49.
Kratochvil et al., "Atomoxetine: a selective noradrenaline reuptake inhibitor for the treatment of attention-deficit/hyperactivity disorder," Expert Opin. Pharmacother. 4(7):1165-1174 (2003).
McKenna et al., "Effect of particle size on the compaction mechanism and tensile strength of tablets," J. Pharm. Pharmacol. Jun. 1982, vol. 34(6), pp. 347-351.
McKetta et al., "Table of Contents," Encyclopedia of Chemical Processing and Design (1989).
McKetta et al., Encyclopedia of Chemical Processing and Design, "Organic Phase Separation Conservation," p. 167 (1989).
Mitsuo et al., Pharmaceutics Manual, 1989, Pharmaceutics Manual, Nanzando Co. Ltd.
Nwokole et al., "Tolerance during 29 days of conventional dosing with cimetidine, mizatidine, famotidine or ranitidine," Aliment. Pharmacol. Ther. 4(Suppl. 1):29-45 (1990) Abstract only.
Observations issued by the European Patent Office on Aug. 16, 2002 regarding European Application No. 0914818 (Applicant Kyowa Hakko Kogyo Co., Ltd.).
Office Action, Mexico patent application No. MX/a/2007/004741, 3 pages, Mexico Patent Office (Oct. 12, 2010).
Oh, International Preliminary Report on Patentability, 5 pages, from International Appl. No. PCT/US2005/037084, United States Patent and Trademark Office, Alexandria, Virginia, USA (mailed Aug. 24, 2007).
Oh, Office Action, 5 pages, U.S. Appl. No. 10/453,848, United States Patent and Trademark Office (Dec. 29, 2005).
Oh, Office Action, 6 pages, U.S. Appl. No. 10/453,848, United States Patent and Trademark Office (Dec. 12, 2007).
Oh, Office Action, 7 pages, U.S. Appl. No. 10/453,848, United States Patent and Trademark Office (Nov. 28, 2006).
Oh, Office Action, 7 pages, U.S. Appl. No. 10/453,848, United States Patent and Trademark Office (Jun. 13, 2007).
Ohira et al., "Effects of Various Histamine $H_2$-Receptor Antagonists on Gastrointestinal Motility and Gastric Emptying," J. Smooth Muscle Res. 29:131-142 (1993).
Opposition Documents related to European Opposition of EP 0914818B1 (Opposition file history as of Mar. 9, 2009, excluding duplicative, purely administrative documents (97 pages total)).
Packard, Advisory Action Before the Filing of an Appeal Brief, 5 pages from U.S. Appl. No. 11/223,819 (mailed Jun. 24, 2010).
Packard, Office Action Summary, 16 pages from U.S. Appl. No. 11/223,819 (mailed Feb. 24, 2009).
Packard, Office Action Summary, 8 pages from U.S. Appl. No. 11/223,819 (mailed Aug. 22, 2008).
Packard, Office Action Summary, 9 pages from U.S. Appl. No. 11/223,819 (mailed Dec. 7, 2009).
Pharmaceutical Excipients, London: Pharmaceutical Press, Electronic Version, 2006, Mannitol.
Pharmaceutical Excipients, London: Pharmaceutical Press, Electronic Version, 2006, Lactose Monohydrate.
Pharmaceutical Excipients, London: Pharmaceutical Press. Electronic Version, 2006, Croscarmellose sodium.
Potenza, Examiner's first report on patent application No. 2005307052, 3 pages, Australia Patent Office (Mar. 15, 2010).
Rankin, International Search Report, 6 pages, PCT International Application No. PCT/US02/39238, European Patent Office (May 8, 2003).
Rudnic et al., "Some Effects of Relatively Low Levels of Eight Tablet Disintegrants on a Direct Compression System," Drug. Dev. Ind. Pharm. 1981, vol. 7(3), pp. 347-358.
Rudnic et al., "Studies of the Utility of Cross Linked Polyvinlpolypyrrolidine as a Tablet Disintegrant," Drug Development and Industrial Pharmacy, 1980, vol. 6, No. 3, pp. 291-309.
Sato et al., "Anticonvulsant effects of tigabine, a new antiepileptic drug: the profile of action in the rat kindling model of epilepsy," Epilepsia 37(Supp. 3):110-111 (1996).

(56) References Cited

OTHER PUBLICATIONS

Schifferer, Communication pursuant to Article 94(3) EPC, 3 pages, from European Patent Appl. No. 05851221.1, European Patent Office, Munich, Germany (mailed Oct. 13, 2009).
Schifferer, Communication, 9 pages, from European Pat. Appl. No. 10184903.2, European Patent Office (Mar. 17, 2011).
Schifferer, International Search Report, 4 pages, from International Appl. No. PCT/US2005/037084, European Patent Office, Rijswijk, The Netherlands (mailed Jun. 1, 2006).
Schifferer, Written Opinion of the International Search Authority, 6 pages, from International Appl. No. PCT/US2005/037084, European Patent Office, Munich, Germany (mailed Jun. 1, 2006).
Shangraw et al., "A new era of tablet disintegrants," Pharm. Technol. 1980, vol. 4(10), pp. 49-57.
Spear, Office Action Summary, 16 pages, from U.S. Appl. No. 10/356,641 (mailed Dec. 8, 2004).
Tirkkonen and Paronen, "Enhancement of drug release from ethylcellulose microcapsules using solid sodium chloride in the wall," Int. J. Pharmaceutics 88:39-51 (1992).
Trottier and Wood, 2005, "Particle Size Measurement," Kirk-Othmer Encyclopedia of Chemical Technology (Extract of 1. Introduction; 2. Data Representation; 4. Measurement Methods; 8. Selection of Equipment).
Ueki et al., "Nizatidine Comparably Enhances Postprandial Gastric Motility to Existing Gastroprokinetics in Dogs," Jpn. Pharmacol. Ther. 28(11):925-930 (2000).
Uhl, International Search Report, 5 pages, International Patent Appl. No. PCT/US2006/016538, European Patent Office (Feb. 27, 2007).
Uhl, Written Opinion of the International Searching Authority, 6 pages, International Patent Appl. No. PCT/US2006/016538, European Patent Office (Feb. 27, 2007).
van Kamp et al., "Improvement by super disintegrants of the properties of tablets containing lactose, prepared by wet granulation," Pharmaceutisch Weekblad Scientific Edition; 1983, vol. 5, pp. 165-171.
Villa, Communication pursuant to Article 94(3) EPC, 3 pages, from European Patent Appl. No. 05818156.1, European Patent Office, Munich, Germany (mailed Jul. 1, 2009).
Villa, Communication pursuant to Article 94(3) EPC, 4 pages, from European Patent Appl. No. 05818156.1, European Patent Office (Feb. 25, 2011).
Villa, European Search Report, 5 pages, from European Patent Appl. No. 11171982.9, European Patent Office, Munich, Germany (mailed Dec. 22, 2011).
Villa, International Search Report, 4 pages, from International Appl. No. PCT/US2005/038328, European Patent Office, Rijswijk, The Netherlands (mailed Sep. 15, 2006).
Villa, Written Opinion of the International Search Authority, 5 pages, from International Appl. No. PCT/US2005/038328, European Patent Office, Munich, Germany (mailed Sep. 15, 2006).
Vromans et al., "Studies on tableting properties of lactose," Pharmaceutisch Weekblad Scientific Edition; 1985, vol. 7, pp. 186-193.
Walsh, Examination Report, 2 pages, from New Zealand Patent Appl. No. 589750, New Zealand Patent Office (Dec. 8, 2010).
Walsh, Examination Report, 2 pages, from New Zealand Patent Appl. No. 554240, New Zealand Patent Office, Wellington, New Zealand (mailed Jun. 9, 2009).
Ware, Office Action Summary, 12 pages, from U.S. Appl. No. 09/147,374 (mailed Oct. 14, 1999).
Ware, Office Action Summary, 6 pages, from U.S. Appl. No. 09/147,374 (mailed Jun. 30, 2002).
Ware, Office Action Summary, 6 pages, from U.S. Appl. No. 09/147,374 (mailed Aug. 29, 2001).
Ware, Office Action Summary, 6 pages, from U.S. Appl. No. 09/147,374 (mailed Jun. 4, 2002).
Ware, Office Action Summary, 8 pages, from U.S. Appl. No. 09/147,374 (mailed Apr. 18, 2001).
Welter, Advisory Action Before the Filing of an Appeal Brief, 4 pages from U.S. Appl. No. 11/248,596 (mailed Oct. 13, 2010).
Welter, Advisory Action Before the Filing of an Appeal Brief, 9 pages from U.S. Appl. No. 11/256,653 (mailed Sep. 27, 2010).
Welter, Office Action Summary, 25 pages from U.S. Appl. No. 11/256,653 (mailed Mar. 18, 2010).
Welter, Office Action Summary, 26 pages from U.S. Appl. No. 11/213,266 (mailed Nov. 13, 2009).
Welter, Office Action Summary, 26 pages from U.S. Appl. No. 11/248,596 (mailed Mar. 19, 2010).
Welter, Office Action Summary, 28 pages from U.S. Appl. No. 11/213,266 (mailed Apr. 6, 2009).
Welter, Office Action Summary, 28 pages from U.S. Appl. No. 11/248,596 (mailed Jul. 10, 2008).
Welter, Office Action Summary, 28 pages from U.S. Appl. No. 11/248,596 (mailed Apr. 29, 2008).
Welter, Office Action Summary, 29 pages from U.S. Appl. No. 11/213,266 (mailed Jul. 10, 2008).
Welter, Office Action Summary, 29 pages from U.S. Appl. No. 11/256,653 (mailed Jul. 10, 2008).
Welter, Office Action Summary, 29 pages from U.S. Appl. No. 11/256,653 (mailed May 12, 2009).
Welter, Office Action Summary, 33 pages from U.S. Appl. No. 11/213,266 (mailed Nov. 12, 2010).
Welter, Office Action, 24 pages, U.S. Appl. No. 12/466,855, United States Patent and Trademark Office (Mar. 17, 2011).
Westerberg, Office Action, 11 pages, U.S. Appl. No. 11/500,892, United States Patent and Trademark Office (Mar. 26, 2010).
Westerberg, Office Action, 11 pages, U.S. Appl. No. 11/500,892, United States Patent and Trademark Office (Dec. 8, 2010).
Yamahara et al., "Effect of release rate on bioavailability of control-release multiple unit dosage forms," Yakuzaigaku 55(2):99-107 (1995).
Yamamoto et al., "The Effects of Nizatidine on the Function of Esophageal Motility in Patients with Gastroesophageal Reflux Disease (GERD)," Jpn. Pharmacol. Ther. 28(5):419-424 (2000).
Young, International Preliminary Examination Report 6 pages, PCT International Application No. PCT/US02/39238, United States and Trademark Office (Apr. 27, 2005).
Young, International Search Report, 2 pages, PCT appl. No. PCT/US11/20493, United States Patent and Trademark Office (mailed Mar. 23, 2011).
Young, Written Opinion of the International Searching Authority, 6 pages, PCT appl. No. PCT/US11/20493, United States Patent and Trademark Office (mailed Mar. 23, 2011).
Young, Written Opinion, 5 pages, PCT International Application No. PCT/US02/39238, United States Patent and Trademark Office (Jan. 13, 2005).
Zheng et al., "Influence of Eudragit® NE 30 D Blended with Eudragit® L 30 D-55 on the Release of Phenylpropanolamine Hydrochloride from Coated Pellets," Drug Development and Industrial Pharmacy 29(3):357-366 (2003).
Zimmer, European Search Report, 3 pages, European patent appl. No. 01103129.1, European Patent Office (Jun. 9, 2011).
Zimmer, International Search Report, 4 pages, PCT International Application No. PCT/US01/04012, European Patent Office (Jun. 19, 2001).

INTRABUCCALLY RAPIDLY DISINTEGRATING TABLET AND A PRODUCTION METHOD OF THE TABLETS

CROSS REFERENCE TO RELATED APPLICATIONS

This application is a continuation of U.S. patent application Ser. No. 13/282,271, filed Oct. 26, 2011, which in turn is a divisional and claims the benefit under 35 U.S.C. §120 of U.S. patent application Ser. No. 10/356,641, filed on Jun. 20, 2003, which is a continuation-in-part of U.S. application Ser. No. 09/147,374, filed on Jun. 4, 1999, now abandoned, which is a National Stage entry of PCT/JP97/02032, filed on Jun. 12, 1997. The entire content of these prior applications is fully incorporated herein by reference.

BACKGROUND OF THE INVENTION

I. Field of the Invention

This invention relates to tablets rapidly disintegrable in the buccal cavity.

II. Prior Art

There are various types of oral administrative medicines: tablets, capsules, granules, powders, syrups and so on. However, such oral administrative medicines have several problems as follows. As to tablets and capsules, for example, it may be hard for aged person or children whose swallowing power is weak to swallow them. And as to granules and powders, they may cause unpleasantness in the mouth after dosage or they may erroneously happen to enter into a respiratory tract or lungs. Further, they can't be taken where there is no water because water is usually required for dosage. As for syrups, it may be difficult for aged persons or children who can not measure them accurately to take them due to the trouble of measuring them for dosage.

On the other hand, solid medicines which can be rapidly dissolved or disintegrated in the buccal cavity can be taken without measuring nor water, so they may be easily taken by such aged persons or children. Further, such solid medicines can be taken without water.

By the way, there have been developed several types of medicines which can be rapidly dissolved or disintegrated in the buccal cavity on dosing.

For instance, in JP-B-62-50445, solid medicines which can be produced from water solution that mainly contains gelatin including an active ingredient by use of freeze drying method are disclosed. And in WO93/12769, solid medicines which can be produced by drying suspension including agar are also disclosed. However, the medicines produced by the abovementioned prior methods do not have enough hardness to be taken by pushing out of PTP packages (Press Through Pack) containing the medicines. And, they require a special pharmaceutical technique and also require an enormous investment in plants and equipments.

JP-A-5-271054 and WO93/157247 disclose production methods of tablets wherein tablets composed of a saccharide are produced in such a manner that a saccharide mixture supplied with appropriate water is compressed at a low pressure and then dried to make solid tablets. However, such methods also require a special pharmaceutical technique and have the fear that powder composing the tablets may be adhered to the surface of a metal mold in compression process under moistening condition. It may be therefore difficult to utilize those methods in manufacturing use in a plant.

SUMMARY OF THE INVENTION

From the several pharmaceutical points of view, the inventors of the present invention have examined intrabuccally rapidly disintegrating tablets which don't require a special pharmaceutical production technique and can be simply and easily produced by a normal equipment. As a result, they have developed, as new pharmaceutical tablets, compressed tablets produced by mixing a sugar alcohol such as D-mannitol and a lactose or a saccharide which have an average particle diameter of not more than 30 μm (first particle), an active ingredient and a disintegrant, by granulating the mixture to obtain a granulated material (second particle), and by compressing the granulated material. The tablets can be disintegrated in a buccal cavity within one minute and have hardness without a trouble for practical use, although it has been considered unable to produce for long time.

The present invention relates to the followings;

(1) An intrabuccally rapidly disintegrating tablet comprising: a sugar alcohol or a saccharide, each of which is first particle having an average particle diameter of not more than 30 μm; an active ingredient; and a disintegrant.

(2) An intrabuccally rapidly disintegrating tablet produced by: growing a powder material into a granulated material with a fixed particle diameter, the powder material comprising a sugar alcohol or a saccharide, each of which is first particle having an average particle diameter of not more than 30 μm; mixing thus obtained granulated material with an active ingredient and a disintegrant; and compressing the mixture into a predetermined shape.

(3) An intrabuccally rapidly disintegrating tablet produced by: growing a mixture of a powder material and an active ingredient into a granulated material with a fixed particle diameter, the powder material comprising a sugar alcohol or a saccharide, each of which is first particle having an average particle diameter of not more than 30 μm; mixing thus obtained granulated material with a disintegrant; and compressing the mixture into a predetermined shape.

(4) An intrabuccally rapidly disintegrating tablet produced by: growing a mixture of a powder material and a disintegrant into a granulated material with a fixed particle diameter, the powder material comprising a sugar alcohol or a saccharide, each of which is first particle having an average particle diameter of not more than 30 μm; mixing thus obtained granulated material with an active ingredient; and compressing the mixture into a predetermined shape.

(5) An intrabuccally rapidly disintegrating tablet produced by: growing a mixture of a powder material, an active ingredient and a disintegrant into a granulated material with a fixed particle diameter, the powder material comprising a sugar alcohol or a saccharide, each of which is first particle having an average particle diameter of not more than 30 μm; and compressing the mixture into a predetermined shape.

(6) The intrabuccally rapidly disintegrating tablet as set forth in the above-mentioned (1)-(5) wherein the tablet is compressed into a predetermined shape after adding a lubricant in the granulated material.

(7) The intrabuccally rapidly disintegrating tablet as set forth in the above-mentioned (1)-(5) wherein the tablet is compressed into a predetermined shape after applying a lubricant on material contacting surfaces of punches and dies of a tabletting machine in advance prior to compression procedure.

(8) The intrabuccally rapidly disintegrating tablet as set forth in the above-mentioned (1)-(5) wherein the tablet contains an active ingredient in the amount of 0.01-30% by weight of the tablet, a disintegrant in the amount of 1-10% by weight of the tablet, a sugar alcohol or a saccharide in the amount of 60-95% by weight of the tablet.

(9) The intrabuccally rapidly disintegrating tablet as set forth in the above-mentioned (1)-(5) wherein the tablet contains a disintegrant in the amount of 1-10% by weight.

(10) The intrabuccally rapidly disintegrating tablet as set forth in the above-mentioned (1)-(5) wherein the sugar alcohol is D-mannitol.

(11) The intrabuccally rapidly disintegrating tablet as set forth in the above-mentioned (1)-(5) wherein the saccharide is a lactose.

(12) The intrabuccally rapidly disintegrating tablet as set forth in the above-mentioned (1)-(5) wherein the disintegrant is at least one selected from the group consisting of crosspovidone, crosscarmellose sodium, or low substituted hydroxypropycellulose.

(13) The intrabuccally rapidly disintegrating tablet as set forth in the above-mentioned (1)-(5) wherein a disintegration time in the buccal cavity of the tablet is not more than 1 minute.

(14) The intrabuccally rapidly disintegrating tablet as set forth in the above-mentioned (1)-(5) wherein the tablet has a hardness of 4 kg and the tablet goes down through a No. 10 mesh wire within 30 seconds when the tablet is placed on the mesh wire and a drop of water is fallen onto the tablet at a speed of 4 ml per minute.

(15) The intrabuccally rapidly disintegrating tablet as set forth in the above-mentioned (1)-(5) wherein the sugar alcohol or the saccharide is prepared in advance to be pulverized into an average particle size of not more than 30 μm.

(16) A production method of an intrabuccally rapidly disintegrating tablet, comprising the steps of:
a) growing a powder material comprising a sugar alcohol or a saccharide, each of which is first particle having an average particle size of not more than 30 μm, into a granulated material with predetermined size;
b) mixing thus obtained granulated material with an active ingredient and a disintegrant, adding a lubricant; and
c) compressing the mixture thus produced as above into a predetermined shape.

(17) A production method of an intrabuccally rapidly disintegrating tablet, comprising the steps of:
a) growing a mixture of a powder material and an active ingredient, the powder material comprising a sugar alcohol or a saccharide, each of which is first particle having an average particle size of not more than 30 μm, into a granulated material with a predetermined size;
b) mixing thus obtained granulated material with and a disintegrant, adding a lubricant; and
c) compressing the mixture thus produced as above into a predetermined shape

(18) A production method of an intrabuccally rapidly disintegrating tablet, comprising the steps of:
a) growing a mixture of a powder material and a disintegrant, the powder material comprising a sugar alcohol or a saccharide, each of which is first particle having an average particle size of not more than 30 μm, into a granulated material with a predetermined size;
b) mixing thus obtained granulated material with an active ingredient, adding a lubricant; and
c) compressing the mixture thus produced as above into a predetermined shape.

(19) A production method of an intrabuccally rapidly disintegrating tablet, comprising the steps of:
a) growing a mixture of a powder material, an active ingredient, and a disintegrant, the powder material comprising a sugar alcohol or a saccharide, each of which is first particle having an average particle size of not more than 30 μm, into a granulated material with a predetermined size;
b) mixing thus obtained granulated material, adding a lubricant; and
c) compressing the mixture thus produced as above into a predetermined shape.

(20) The production method of an intrabuccally rapidly disintegrating tablet as set forth in the above-mentioned (16)-(19) wherein the sugar alcohol or the saccharide is prepared in advance to be pulverized into an average particle size of not more than 30 μm.

(21) A production method of an intrabuccally rapidly disintegrating tablet, comprising the steps of:
a) growing a powder material comprising a sugar alcohol or a saccharide, each of which is first particle having an average particle size of not more than 30 μm, into a granulated material with a predetermined size;
b) mixing thus obtained granulated material with an active ingredient and a disintegrant, without adding a lubricant; and further comprising the steps for compressing the mixture thus produced as above;
c) spraying a lubricant on material contacting surfaces of punches and dies of a tabletting machine as a pre-compression step; and
d) compressing the mixture supplied to the die of the tabletting machine into a predetermined shape.

(22) A production method of an intrabuccally rapidly disintegrating tablet, comprising the steps of:
a) growing a mixture of a powder material and an active ingredient, the powder material comprising a sugar alcohol or a saccharide, each of which is first particle having an average particle size of not more than 30 μm, into a granulated material with a predetermined size;
b) mixing thus obtained granulated material with a disintegrant, without adding a lubricant; and
further comprising the steps for compressing the mixture thus produced as above;
c) spraying a lubricant on material contacting surfaces of a punches and dies of a tabletting machine as a pre-compression step; and
d) compressing the mixture supplied to the die of the tabletting machine into a predetermined shape.

(23) A production method of an intrabuccally rapidly disintegrating tablet, comprising the steps of:
a) growing a mixture of a powder material and a disintegrant, the powder material comprising a sugar alcohol or a saccharide, each of which is first particle having an average particle size of not more than 30 μm, into a granulated material with a predetermined size;
b) mixing thus obtained granulated material with an active ingredient, without adding a lubricant; and
further comprising the steps for compressing the mixture thus produced as above;
c) spraying a lubricant on material contacting surfaces of punches and dies of a tabletting machine as a pre-compression step; and
d) compressing the mixture supplied to the die of the tabletting machine into a predetermined shape.

(24) A production method of an intrabuccally rapidly disintegrating tablet, comprising the steps of:
a) growing a mixture of a powder material, an active ingredient and a disintegrant, the powder material comprising a sugar alcohol or a saccharide, each of which is first particle having an average particle size of not more than 30 μm, into a granulated material with a predetermined size;
b) mixing thus obtained granulated material without adding a lubricant; and further comprising the steps for compressing the mixture thus produced as above into a predetermined shape;

c) spraying a lubricant on material contacting surfaces of punches and dies of a tabletting machine as a pre-compression step; and d) compressing the mixture supplied to the die of the tabletting machine into a predetermined shape.

(25) The production method of an intrabuccally rapidly disintegrating tablet as set forth in the above-mentioned (21)-(24) wherein the sugar alcohol or the saccharide is prepared in advance to be pulverized into an average particle size of not more than 30 μm.

(26) An intrabuccally rapidly disintegrating tablet comprising: a sugar alcohol or a saccharide of which average particle size is not more than 30 μm as a main ingredient; an active ingredient; and a disintegrant, wherein the main ingredient is contained in the amount of 60-95% by weight of the tablet and the disintegrant is contained in the amount of 1-10% by weight of the tablet.

(27) The intrabuccally rapidly disintegrating tablet as set forth in the above-mentioned (26), the tablet is produced by: granulating a mixture of the main ingredient, the active ingredient and the disintegrant; mixing thus granulated material with a fixed amount of lubricant and a required adjuvant; and compressing thus mixed material into a predetermined shape.

(28) The intrabuccally rapidly disintegrating tablet as set forth in the above-mentioned (26), the tablet is produced by: granulating a mixture of the main ingredient, the active ingredient and the disintegrant; mixing thus granulated material without adding a lubricant; applying a lubricant on punches and dies of a tabletting machine; and compressing thus mixed material into a predetermined shape.

(29) The intrabuccally rapidly disintegrating tablet as set forth in the above-mentioned (26)-(28) wherein the main ingredient is either one of D-mannitol or a lactose.

(30) The intrabuccally rapidly disintegrating tablet as set forth in the above-mentioned (26)-(29) wherein the disintegrant is at least one selected from the group consisting of crosspovidone, crosscarmellose sodium, or low substituted hydroxypropycellulose.

(31) The intrabuccally rapidly disintegrating tablet as set forth in the above-mentioned (30) wherein the tablet contains 1 to 30 mg disintegrant for one dosage.

(32) A production method of an intrabuccally rapidly disintegrating tablet comprising a sugar alcohol or a saccharide of which average particle size is not more than 30 μm as a main ingredient, an active ingredient, and a disintegrant wherein the main ingredient is contained 60-95% by weight of the tablet and the disintegrant is contained 1-10% by weight of the tablet, comprising the steps of: producing a mixture of the main ingredient, the active ingredient and the disintegrant; mixing the mixture with a fixed amount lubricant and a required adjuvant; and compressing thus mixed material into a predetermined shape.

(33) A production method of an intrabuccally rapidly disintegrating tablet comprising a sugar alcohol or a saccharide of which average particle size is not more than 30 μm as a main ingredient, an active ingredient, and a disintegrant wherein the main ingredient is contained in the amount of 60-95% by weight of the tablet and the disintegrant is contained in the amount of 1-10% by weight of the tablet, comprising the steps of: producing a mixture of the main ingredient, the active ingredient and the disintegrant; granulating the mixture into a predetermined size; mixing thus granulated material with a required adjuvant without adding a lubricant; applying a lubricant on punches and dies of a tabletting machine; and compressing thus mixed material into a predetermined shape.

Generally, first particle refers to single particle of raw material. In this specification, first particle means a single particle of raw material in nature and doesn't mean particle of an aggregation. Generally, second particle refers to particle in which special process is executed for the first particle. Second particle in this specification means particle after some process such as granulation is executed, namely particle of granulated material which is an aggregation of first particle (for example granule).

The object of the present invention is to provide an intrabuccally rapidly disintegrating tablet which includes a sugar alcohol or a saccharide of which is first particle having not more than 30 μm in average particle size, further includes an active ingredient and a disintegrant and which is produced by compressing into a predetermined shape.

The method of producing the intrabuccally rapidly disintegrating tablet according to the present invention includes an internal lubrication method in which a powder material and a lubricant are mixed before compression and an external lubrication method in which a lubricant is applied on punches and dies of a tabletting machine before compression.

D-mannitol can be used as a sugar alcohol in the present invention, and a lactose can be used as a saccharide. At least one kind of a sugar alcohol or a saccharide is used.

As active ingredients, followings are used, but other ingredients for oral administration can be also used.

<drug for central nervous system> hyprotics, anxiolytics . . . amobarbital, alprazolam, flurazepam hydrochloride, diazepam, and so on NTHEs/antiepileptic . . . valproate sodium, nitrazepam, phenytoin, and so on analgesic antipyretic agent . . . aspirin, acetaminophen, ibuprofen, diclofenac sodium, ethenzamide, indometacin and so on drug for Pakinson's disease . . . levodopa, amantadine hydrochloride, trihexyphenidyl hydrochloride, piroheptine hydrochloride, and so on psychoneurosis agent . . . etizolam, amitriptyline hydrochloride, sulpiride, and so on <Drug for Peripheral Nervous System> skeletal muscle relaxant chlorphenesin carbamate, chlormezanone, and so on autonomic nervous agent . . . valethamate bromide, tofisopam, and so on antispasmodic . . . afloqualone, and so on <Drug for Circulatory> cardiac . . . ubidecarenon, aminophylline, etilefrine hydrochloride, and so on antiarrhythmic agents . . . atenolol, pindolol, and so on diuretic . . . spironolactone, trichlormethiazide, furosemide, and so on antihypertensive agent . . . todrazine hydrochloride, nicardipine hydrochloride, hydralazine hydrochloride, and so on angiotonic . . . dihydroergotamine mesilate and so on vasodilator . . . benidipine hydrochloride, diltiazem hydrochloride, isosorbide dinitrate, and so on hyperlipemia . . . clinofibrate, nicomol, and so on others . . . flunarizine hydrochloride, meclofenoxate hydrochloride, cinnarizine, and so on <Antidiarrhea> antidiarrhoeic . . . loperamide hydrochloride, dimeticone, and so on drug for peptic ulcer . . . azulene, L-glutamine, aceglutamide aluminium, cetraxate hydrochloride, cimetidine, and so on cholagogue . . . anethoitrithion, chenodeoxycholic acid, and so on others . . . donperidone, trimebutine maleate, metoclopramide, cisapride, and so on <Metabolic Drug> vitamin . . . alfacarcidol, tiamine hydrochloride, cobamide, vitaroxin, riboflavin butyrate, ascorbic acid, phytonadione, and so on diabetes mellitus . . . agent glybuzole, tolbutamide, and so on <Antiallergies> antihistamine . . . homochlorcyclizine hydrochloride, clemastine fumarate, chlorpheniramine maleate, and so on others . . . oxatomide, ketotifen fumarate, azelastin hydrochloride, and so on <Antineoplastics> metabolic antagoism agent . . . fluorouracil, tegafur, and so on

<Antibiotics> paromomycin sulfate, amoxicillin, cefaclor, cefalexin, acetylspiramycin, minocycline hydrochloride Wherein such as crosspovidone, cross sodium carboxymethyl cellulose, low substituted hydroxypropylcellulose or the like, which are widely used for drugs and food can be used as a disintegrant. At least one kind of disintegrant is used.

Next, a production method of tablets according to the present invention will be described hereinafter.

The tablets of the present invention can be obtained by compressing and tabletting after granulating a mixed powdered components containing a sugar alcohol or a saccharide of which is first particle having an average particle diameter of not more than 30 μm, an active ingredient, and a disintegrant by means of a hammer mill, a jet mill or the like.

The amount of sugar alcohol or saccharide is preferably about 60-95 weight % in the amount of a resulting tablet, more preferably about 80-95 weight % of a resulting tablet.

The amount of active ingredient is different depending on the kind and dosage amount of active ingredient, however, about 0.01-30 weight % in the amount of a resulting tablet is preferable, and more preferably about 0.01-10 weight % of a resulting tablet.

The amount of disintegrant present is preferably about 1-30 mg per dosage, and more preferably about 1-10 weight % in the amount of a resulting tablet.

A granulation method isn't limited, however a wet granulation method using purified water, ethanol or the like can be preferably used. In the method, for example, granulation can be executed by means of a fluid-bed granulator, a rotary stirring granulator or an extruding granulator. The granulated material is dried, mixed with a lubricant, and thereafter compressed into a predetermined shape. Binders, sour agents, foaming agents, sweetening agents, flavoring agents, or colorants can be added as additives. Otherwise, a dry granulation method may be used.

As a lubricant, such as magnesium stearate, calcium stearate stearic aid, stearic acid, stearyl alcohol, sucrose esters of fatty acid, talc, light anhydrous silicic acid, or like present. Binders present, for example, hydroxypropyl-cellulose, polyvinylphrrolidone, hydroxypropyl-methylcellulose, partially saponificated polyvinyl alcohol, methyl cellulose, pullulan or the like. Sour agents present citric acid, malic acid, adipic acid, ascorbic acid, and the like. Foaming agents are sodium bicarbonate, sodium carbonate, calcium carbonate, and the like. Sweetening agents are Aspartame™, saccharin, glycyrrhizic acid or the like. Flavoring agents are lemon, orange, pine, mint, menthol or the like. Colorants are yellow iron sesquioxide, red iron sesquioxide, tar color or the like.

The amount of lubricant is preferably about 0.01-2 weight % in the amount of a tablet and more preferably about 0.01-0.5 weight %.

Such an intrabuccally rapidly disintegrating tablet of the present invention can be produced by an internal lubrication method wherein a lubricant is internally contained in the tablet by mixing a lubricant into the granule prior to compression. Further, it can be produced also by an external lubrication method wherein a lubricant isn't included in the tablet and is externally attached to the outer surface of the tablet by applying a lubricant onto the material contacting surfaces of punches and dies of a tabletting machine.

In both of the internal lubrication method and the external lubrication method, there are several compression methods: after granulating a sugar alcohol or a saccharide, an active ingredient and a disintegrant are mixed and compression is executed; after granulating a sugar alcohol or a saccharide and an active ingredient, a disintegrant is mixed and compression is executed; after granulating a sugar alcohol or a saccharide and a disintegrant, an active ingredient is mixed and compression is executed; after granulating a sugar alcohol or a saccharide, an active ingredient and a disintegrant, compression is executed.

Although a tabletting method isn't limited in the present invention, a rotary tabletting machine, a hydraulic press machine or a single punch tabletting machine which have high productivity can be more preferably used.

The shape of tablets obtained in the present invention can be pills or other shapes such as normal R surface (concave plane surface) tablets, a sugar coated R surface tablets, tablets with square edges, tablets with rounded edges, or tablets with two R surfaces, or the like.

The tablet may be a dividable tablet with a dividing line.

DESCRIPTION OF THE PREFERRED EMBODIMENTS

The present invention will be concretely explained according to preferable embodiments and comparative embodiments as described in following experimental data.

[Comparison 1]

1890 g of D-mannitol (Towa Kasei Co., Ltd., average particle diameter of about 60 μm) and 100 g of crosspovidone (POLYPLASDONE XL-10: GAF Co., Ltd.) were fed in a fluid-bed granulation dryer (Gratt Co., Ltd.: WSG-type 5), and purified water was sprayed in the dryer to produce a granulated material and the material thus grown after the granulation was dried. 10 g of magnesium stearate was added and mixed with the granulated material, and they were compressed and tabletted with a rotary tabletting machine (Kikusui Co., Ltd., clean press collect type 12) in which the tabletting conditions were as follows; tablet weight was 200 mg, a metal mold was 8 mm diameter flat-type, and compression pressure was varied such as 150 kg, 300 kg, 450 kg, 600 kg, and 800 kg to produce resulting tablets.

[Embodiment 1]

D-mannitol (Towa Kasei Co., Ltd.: average particle diameter of about 60 μm) was previously ground by a jet mill (Japan Pneumatic Co., Ltd.: type PJM-I-1.5) and the pulverized D-mannitol with average particle diameter of 20 μm was obtained. 1890 g of the pulverized D-mannitol and 100 g of crosspovidone (POLYPLASDONE XL-10: GAF Co., Ltd.) were fed in a fluid-bed granulation dryer (Gratt Co., Ltd.: WSG-type 5), purified water was sprayed, and a granulated material was obtained after granulation and drying process. 10 g of magnesium stearate was added and mixed with the granulated material and they were compressed and tabletted with a rotary tabletting machine (Kikusui Co., Ltd., clean press collect type 12) in which tabletting conditions were the same as that in the Comparison 1.

[Comparison 2]

100 g of donperidone, gastrointestinal motility improvement agent, 1790 g of lactose (DMV Co., Ltd.: average particle diameter of about 80 μm) and 100 g of crosspovidone (POLYPLASDONE XL-10: GAF Co., Ltd.) were fed in a fluid-bed granulation dryer (Gratt Co., Ltd.: WSG-type5), purified water was sprayed in the dryer, and a granulated material was obtained after granulation and drying process. 10 g of magnesium stearate was added and mixed with the granulated material and they were compressed and tabeletted with a rotary tabletting machine (Kikusui Co., Ltd.,: CLEAN PRESS COLLECT type 12) in which tabletting conditions were the same as that in the Comparison 1.

[Embodiment 2]

Lactose (DMV Co., Ltd.: average particle diameter of about 80 μm) was previously ground by a jet mill (Japan Pneumatic Co., Ltd.: type PJM-I-1.5) to produce pulverized lactose with average particle diameter of 15 μm. 1790 g of the pulverized lactose, 100 g of donperidone, and 100 g of crosspovidone (POLYPLASDONE XL-10: GAF Co., Ltd.) were fed in a fluid-bed granulation dryer (Gratt Co., Ltd.: WSG-type 5), purified water was sprayed in the dryer, and a granulated material was obtained after granulation and drying process. 10 g of magnesium stearate was added and mixed with the granulated material and they were compressed and tabeletted with a rotary tabletting machine (Kikusui Co., Ltd., CLEAN PRESS COLLECT TYPE 12) in which tabletting conditions were the same as that in the Comparison 1.

[Embodiment 3]

The granulated material obtained in the Embodiment 1 was tabletted under the condition that the tablet weight was 200 mg and the compression pressure was 50 kg/c m$^2$, and a little magnesium stearate was coated on a metal mold (8 mm diameter flat-type) and dies of a hydraulic press machine (Riken Seiki Co., Ltd.: type P-1B) to obtain a tablet.

Table 1 shows the evaluation result of the hardness and disintegration time of the tablets obtained by the Embodiments 1 and 2 and the Comparisons 1 and 2.

The hardness of the tablets was measured by a tablet destructive strength measuring instrument (Toyama Sangyo Co., Ltd. TH-203CP type), and as for the disintegration time test of the tablets, a unique measuring method (called as DW (Drops Water) method hereinafter) was used because a disintegration test method according to the Japanese Pharmacopoeia is different from the actual condition in the buccal cavity. In the DW method, while resulting tablets were placed on a No. 20 wire cloth, onto which water was dropped at a speed of 4 ml/min., and the time till the tablets fall down through the wire cloth was measured as the disintegration time.

TABLE 1

| sample | | compression pressure | | | | |
|---|---|---|---|---|---|---|
| | | 150 kg | 300 kg | 450 kg | 600 kg | 800 kg |
| Comparison 1 | Hardness | hard to be tableted | hard to be tableted | hard to be tableted | 1.9 kgf | 2.3 kgf |
| | disintegration | — | — | — | 20 sec. | 22 sec. |
| Embodiment 1 | Hardness | 1.9 kgf | 3.9 kgf | 5.1 kgf | 6.2 kgf | 7.3 kgf |
| | disintegration | 10 sec. | 15 sec. | 16 sec. | 19 sec. | 27 sec. |
| Comparison 2 | Hardness | hard to be tableted | hard to be tableted | hard to be tableted | 1.5 kgf | 2.1 kgf |
| | disintegration | — | — | — | 18 sec. | 21 sec. |
| Embodiment 2 | Hardness | 1.6 kgf | 4.0 kgf | 4.9 kgf | 5.8 kgf | 6.5 kgf |
| | disintegration | 10 sec. | 16 sec. | 20 sec. | 25 sec. | 29 sec. |

In the Comparisons 1 and 2, it was found that it was hard to mold a tablet by adding under 450 kg compression pressure but it was possible to mold a tablet by adding more than around 600 kg compression pressure, while the hardness of the resulting tablets wasn't enough to practical use.

In the Embodiments 1 and 2, it was found that the tablet hardness enough for practical use could be obtained by adding more than 300 kg compression pressure and its disintegration time was very fast.

When the resulting tablet produced at 450 kg compression pressure according to the Embodiment 1 was dosed, the tablet was disintegrated at 10 seconds in the buccal cavity.

On the other hand, such resulting tablets with less than 30 seconds of the disintegration time of which testing was conducted in the above mentioned DW method were dissolved within 10 seconds in the buccal cavity, and represented such rapid disintegration speed that hasn't been experienced as a prior disintegrating tablets.

The tablets obtained by the Embodiments 3 were also measured of its hardness and disintegration time in the same way as above mentioned. As the result, the resulting tablets had enough hardness of about 6.5 kgf and its disintegration time was 10 seconds.

[Embodiment 4]

D-mannitol with average particle diameter of 60 μm (Towa Kasei Co., Ltd.) was previously ground by a jet mill (Japan Pneumatic Co., Ltd.: type PJM-I-1.5) to obtain D-mannitol with average particle diameter of 15 g m as first particle. D-mannitol thus pulverized of 1880 g by weight and crosspovidone (POLYPLASDONE XL-10: ISP Co., Ltd.) of 100 g by weight were fed into a mixing granulator (Powrex Corporation: type VG-25), mixed with each other, and then the mixture was subjected to granulation with purified water for growing. Thereafter, the granulated material thus grown was dried by a fluid bed dryer to obtain a granulated material with average particle diameter of about 342 μm as second particle. Then 20 g of magnesium stearate was added into the granulated material and 200 g of the mixed granulated material were compressed and tabletted with a rotary tabletting machine (CLEAN PRESS COLLECT TYPE 12, 8 mmφ flat mold, Kikusui Co., Ltd.) at a pressure of 500 kg.

[Embodiment 5]

Second particle with average particle diameter of 334 μm as a granulated material was produced from the first particle with average particle diameter of about 30 μm and a tablet was obtained by executing compressing and tabletting as in the same manner as in the Embodiment 4.

[Comparison 3]

Second particle with average particle diameter of 315 μm as a granulated material was produced from the first particle with average particle diameter of about 60 μm and a tablet was obtained by executing compressing and tabletting as in the same manner as in the Embodiment 4.

[Embodiment 6]

Second particle with average particle diameter of 158 μm as a granulated material was produced from the first particle with average particle diameter of about 15 μm and a tablet was obtained by executing compressing and tabletting as in the same manner as in the Embodiment 4.

[Embodiment 7]

Second particle with average particle diameter of 554 μm as a granulated material was produced from the first particle with average particle diameter of about 15 μm and a tablet was obtained by executing compressing and tabletting as in the same manner as in the Embodiment 4.

[Comparison 4]

D-mannitol with average particle diameter of 60 μm (Towa Kasei Co., Ltd.) was previously ground by a jet mill (Japan Pneumatic Co., Ltd.: type PJM-I-1.5) to obtain D-mannitol with average particle diameter of 15 μm as first particle.

D-mannitol thus pulverized of 1880 g by weight and crosspovidone (POLYPLASDONE XL-10: ISP Co., Ltd.) of 100 g by weight were fed into a mixing granulator (Powrex Corporation: type VG-25), and mixed with each other, then the mixture was subjected to granulation with purified water with 40 g of polyvinyl-pyrrolidone K30 dissolved for growing to obtain a granulated material. Then the granulated material thus grown was dried by a fluid bed dryer, thereby producing a granulated material with average particle diameter of about 350 μm as second particle. Thereafter, 20 g of magnesium stearate was added into the granulated material and 200 mg of the mixed granulated material was compressed and tabletted with a rotary tabletting machine (CLEAN PRESS COLLECT TYPE 12, 8 mmφ flat mold, Kikusui Co., Ltd.) under a pressure of 500 kg to produce a resulting tablet with a specific shape.

[Comparison 5]

Second particle with average particle diameter of 325 μm as a granulated material was produced from the first particle with average particle diameter of about 60 μm and a tablet was produced by executing compressing and tabletting as in the same manner as in Comparison 4.

[Comparison 6]

1780 g of D-mannitol with average particle diameter of 60 μm was fed into a mixing granulator (Powrex Corporation: type VG-25), was subjected to granulation with purified water being dissolved with 200 g of maltose for growing, and then dried to obtain a granulated material with average particle diameter of about 333 μm as second particle. Thereafter, 20 g of magnesium stearate was added into the granulated material and 200 mg of the mixed granulated material was compressed and tabletted with a rotary tabletting machine (CLEAN PRESS COLLECT TYPE 12, 8 mmφ flat mold, Kikusui Co., Ltd.) under a pressure of 500 kg to produce a resulting tablet with a specific shape.

[Comparison 7]

D-mannitol with average particle diameter of 60 μm and crosspovidone (POLYPLASDONE XL-10: ISP Co., Ltd.) of 100 g by weight were fed into a mixing granulator (Powrex Corporation: type VG-25), mixed with each other, and then the mixture was subjected to granulation with purified water with 200 g of maltose dissolved for growing, and then dried to obtain a granulated material with average particle diameter of about 339 μm as second particle. Thereafter, 20 g of magnesium stearate was added into the granulated material and 200 g of the mixed granulated material was compressed and tabletted with a rotary tabletting machine (CLEAN PRESS COLLECT TYPE 12, 8 mmφ flat mold, Kikusui Co., Ltd.) with a pressure of 500 kg.

[Comparison 8]

D-mannitol with average particle diameter of 60 μm (Towa Kasei Co., Ltd.) was previously ground by a jet mill (Japan Pneumatic Co., Ltd.: type PJM-I-1.5) to obtain D-mannitol with average particle diameter of 15 μm as first particle. D-mannitol of 1840 g thus pulverized, crosspovidone (POLYPLASDONE XL-10: GAF Co., Ltd.) of 100 g were fed into a mixing granulator (Powrex Corporation: type VG-25) to be mixed with each other, and the mixture was subjected to granulation with purified water dissolving 40 g of hydroxypropylcellulose (L-HPC, Shin-Etsu Chemical Co., Ltd.) for growing. Then 20 g of magnesium stearate was added into the granulated material and 200 mg of the mixed material was compressed and tabletted with a rotary tabletting machine (CLEAN PRESS COLLECT TYPE 12, 8 mmφ flat mold, Kikusui Co., Ltd.) with a pressure of 500 kg to obtain a resulting tablet with a specific shape.

The intrabuccal method in the table 2 was measured as follows: Each one of five healthy adults took one tablet in the mouth and the time the tablet was dissolved in the buccal cavity with saliva was measured. The average value of five persons was calculated and considered as disintegration time in the buccal cavity.

TABLE 2

Effect of Particle Size on the hardness of resulting tablet

| | 1st particle | 2nd particle | hardness (kg) | disintegration time (sec) | | |
|---|---|---|---|---|---|---|
| | | | | intrabuccal | DW | JP |
| Embodiment 4 | 15 | 342 | 5.2 kg | 9 | 9 | 4 |
| Embodiment 5 | 30 | 334 | 3.5 | 8 | 10 | 5 |
| Comparison 3 | 60 | 315 | 1.2 | 10 | 15 | 7 |
| Embodiment 6 | 15 | 158 | 5.5 | 8 | 8 | 5 |
| Embodiment 7 | 15 | 554 | 5.6 | 10 | 7 | 5 |
| Comparison 4 | 15 | 350 | 4.9 | 350 | 152 | 139 |
| Comparison 5 | 60 | 325 | 3.5 | 303 | 146 | 121 |
| Comparison 6 | 60 | 333 | 3.5 | 286 | 125 | 105 |
| Comparison 7 | 60 | 339 | 4.1 | 215 | 99 | 95 |
| Comparison 8 | 15 | 350 | 4.3 | 101 | 76 | 64 |

Preparation using a saccharide or a sugar alcohol which is first particle having an average particle diameter not more than 30 μm could obtain a practical tablet hardness and rapid disintegration time despite of the size of second particle. On the other hand, if a saccharide or a sugar alcohol of which average particle diameter had 60 μm was used, rapid disintegration time was achieved but enough tablet hardness wasn't obtained. Accordingly it was found that the size of first particle, not secondary particle, was important in order to obtain enough tablet hardness and rapid disintegration.

Comparing with disintegration time in a buccal cavity, that by DW method and that by the Japanese Pharmacopeia (JP) method, the tablet showing about 10 seconds of disintegration time in a buccal cavity showed the same disintegration time in DW method and the JP method. However, the tablet showing more than 100 seconds of disintegration time in the buccal cavity showed faster disintegration time in DW method and the JP method than that in the buccal cavity. Comparing DW method and the JP method, DW method showed disintegration time closer to that in the buccal cavity. The tablet showing about 60 seconds of disintegration time in the JP method required about 100 seconds to be disintegrated in the buccal cavity, namely it couldn't be rapidly disintegrated in the buccal cavity.

[Embodiment 8]

D-mannitol with average particle diameter of 60 μm (Towa Kasei Co., Ltd.) was previously ground by a jet mill (Japan Pneumatic Co., Ltd.: type PJM-I-1.5) to obtain D-mannitol with average particle diameter of 20 μm as first particle D-mannitol thus pulverized of 1710 g, donperidone of 170 g, and cross carmellose sodium of 100 g (Ac-Di-Sol, Asahi Kasei Corporation) were fed into a mixing granulator (Powrex Corporation: type VG-25) to be mixed with each other, and the mixture was subjected to granulation with purified water for growing. Thereafter the granulated material thus grown was dried by a fluid bed dryer and classified by a No. 20 wire mesh. Then 20 g of magnesium stearate was added into the granulated material and 120 mg of thus obtained material, was compressed and tabletted with a rotary tabletting machine (CLEAN PRESS COLLECT TYPE 12, 8 mmϕ flat mold, Kikusui Co., Ltd.) with a pressure of 500 kg to obtain a resulting tablet of which hardness was 4.2 kg, disintegration time in the buccal cavity was 28 seconds and disintegration time by DW method was 26 seconds.

[Embodiment 9]

D-mannitol with average particle diameter of 60 μm (Towa Kasei Co., Ltd.) was previously ground by a jet mill (Japan Pneumatic Co., Ltd.: type PJM-I-1.5) to obtain D-mannitol with average particle diameter of 15 μm as first particle. D-mannitol of 1710 g thus pulverized, donperidone of 170 g, and low substituted hydroxypropylcellulose of 100 g (L-HPC, Shin-Etsu Chemical Co., Ltd.) were fed into a mixing granulator (Powrex Corporation: type VG-25) to be mixed with each other, and the mixtures was subjected to granulation with purified water for growing. Thereafter, the granulated material was dried by a fluid bed dryer and classified by a No. 20 wire mesh. Then 20 g of magnesium stearate was added into the granulated material and 120 mg of thus obtained material was compressed and tabletted with a rotary tabletting machine (CLEAN PRESS COLLECT TYPE 12, 8 mmϕ flat mold, Kikusui Co., Ltd.) with a pressure of 500 kg to obtain a resulting tablet of which hardness was 5.0 kg, disintegration time in the buccal cavity was 30 seconds and disintegration time by DW method was 21 seconds.

[Embodiment 10]

D-mannitol (average particle diameter: 65 μm, Towa Kasei Co., Ltd.) was previously ground by a jet mill (Japan Pneumatic Co., Ltd.: type PJM-I-1.5) to obtain D-mannitol with average particle diameter of 25 μm. D-mannitol thus pulverized of 1790 g and donperidone of 100 g were fed into a mixing granulator (Powrex Corporation: type VG-25) to be mixed with each other, and the mixture was subjected to granulation with purified water for growing. Thereafter, the granulated material thus grown was dried by a fluid bed dryer (Gratt Co., Ltd.: WSG-type 5) and classified by a No. 20 wire mesh. Then 1512 g of thus obtained granulated material, 80 g of crosspovidone (POLYPLASDONE XL-10: GAF Co., Ltd.) and 8 g of magnesium stearate were mixed and compressed to be tabletted with a rotary tabletting machine (CLEAN PRESS COLLECT TYPE 12, Kikusui Co., Ltd.). The tabletting conditions were such that the weight of tablet was 200 mg, the mold was 8 mm diameter and flat type and the tabletting pressure was 800 kg. The obtained tablet had 5.7 kgf of hardness and 12 seconds of disintegration time by a DW method. The actual disintegration time in the buccal cavity was about 10 seconds.

[Embodiment 11]

1790 g of pulverized D-mannitol which had been obtained like in the Embodiment 10 was fed into a mixing granulator (Powrex Corporation: type VG-25), and mixed with each other, then the mixture was subjected to granulation with purified water for growing. Thereafter, the granulated material thus grown was dried by a fluid bed dryer (Gratt Co, Ltd.: WSG-type 5) and classified by a No. 20 wire mesh. Then 1432 g of thus obtained granulated material, 80 g of donperidone as active ingredient, 80 g of crosspovidone, 8 g of magnesium stearate were mixed and compressed to be tabletted with a rotary tabletting machine (CLEAN PRESS COLLECT TYPE 12, Kikusui Co., Ltd.). The tabletting conditions were the same as the Embodiment 10. The obtained tablet had 5.2 kgf of hardness and 14 seconds of disintegration time by a DW method. The actual disintegration time in the buccal cavity was about 10 seconds.

[Embodiment 12]

1790 g of pulverized D-mannitol which had been obtained like in the Embodiment 10 and 100 g of crosspovidone were fed into a mixing granulator (Powrex Corporation: type VG-25), and mixed with each other, then the mixtures was subjected to granulation with purified water for growing. Thereafter, the granulated material thus grown was dried by a fluid bed dryer (Gratt Co., Ltd.: WSG-type 5) and classified by a No. 20 wire mesh. Then 1512 g of thus obtained granulated material, 80 g of donperidone as active ingredient, 8 g of magnesium stearate were mixed and compressed to be tabletted with a rotary tabletting machine (CLEAN PRESS COLLECT TYPE 12, Kikusui Co., Ltd.). The tabletting conditions were the same as the Embodiment 10. The obtained tablet had 5.9 kg f of hardness and 12 seconds of disintegration time by DW method. The actual disintegration time in the buccal cavity was about 10 seconds.

[Embodiment 13]

1790 g of pulverized D-mannitol which had been obtained like in the Embodiment 10, 100 g of donperidone as active ingredient and 100 g of crosspovidone were fed into a mixing granulator (Powrex Corporation: type VG-25), and mixed with each other, then the mixture was subjected to granulation with purified water for growing. Thereafter the granulated material thus grown was dried by a fluid bed dryer (Gratt Co., Ltd.: WSG-type 5) and classified by a No. 20 wire mesh. Then 1592 g of thus obtained granulated material, 8 g of magnesium stearate were mixed and compressed to be tabletted with a rotary tabletting machine (CLEAN PRESS COLLECT TYPE 12, Kikusui Co., Ltd.). The tabletting conditions were the same as the Embodiment 10. The obtained tablet had 6.0 kgf of hardness and 15 seconds of disintegration time by DW method. The actual disintegration time in the buccal cavity was about 10 seconds.

[Embodiment 14]

1790 g of pulverized D-mannitol which had been obtained like in the Embodiment 10, 100 g of donperidone as active ingredient and 100 g of cross carmellose sodium (Ac-Di-Sol, Asahi Kasei Corporation) were fed into a mixing granulator (Powrex Corporation: type VG-25), and mixed with each other, then the mixture was subjected to granulation with purified water for growing. Thereafter the granulated material thus grown was dried by a fluid bed dryer (Gratt Co., Ltd.: WSG-type 5) and classified by a No. 20 wire mesh. Then 1592 g of thus obtained granulated material, 8 g of magnesium stearate were mixed and compressed to be tabletted with a rotary tabletting machine (CLEAN PRESS COLLECT TYPE 12, Kikusui Co., Ltd.). The tabletting conditions were the same as the Embodiment 10. The obtained tablet had 4.5 kgf of hardness and 26 seconds of disintegration time by DW method. The actual disintegration time in the buccal cavity was about 20 seconds.

[Embodiment 15]

1790 g of pulverized D-mannitol which had been obtained like in the Embodiment 10, 100 g of donperidone as active ingredient and 100 g of low substituted hydroxypropylcellulose (L-HPC, Shin-Etsu Chemical Co. Ltd.) were fed into a mixing granulator (Powrex Corporation: type VG-25), and mixed with each other, then the mixture was subjected to granulation with purified water for growing. Thereafter, the granulated material thus grown was dried by a fluid bed dryer (Gratt Co., Ltd.: WSG-type 5) and classified by a No. 20 wire mesh. Then 1592 g of thus obtained granulated material, 8 g of magnesium stearate were mixed and compressed to be tabletted with a rotary tabletting machine (CLEAN PRESS COLLECT TYPE 12, Kikusui Co., Ltd.). The tabletting conditions were the same as the Embodiment 10.

The obtained tablet had 6.2 kgf of hardness and 25 seconds of disintegration time by W method. The actual disintegration time in the buccal cavity was about 20 seconds.

[Embodiment 16]

1790 g of pulverized D-mannitol which had been obtained like in the Embodiment 10, 100 g of donperidone as active ingredient and 100 g of crosspovidone were fed into a mixing granulator (Powrex Corporation: type VG-25), and mixed with each other, then the mixture was subjected to granulation with purified water for growing. Thereafter, the granulated material thus grown was dried by a fluid bed dryer (Gratt Co., Ltd.: WSG-type 5) and classified by a No. 20 wire mesh. Thus obtained granulated material was tabletted with a rotary tabletting machine (Hata Seisakusho, Type AP-15) with a pressure of 500 kg while spraying stearate magnesium from a lubricant spray attached to the tabletting machine. The obtained tablet had 6.7 kgf of hardness and 12 seconds of disintegration time by a DW method. The actual disintegration time in the buccal cavity was about 6 seconds.

According to the above-mentioned experimental data, it has been confirmed that the intrabuccally rapidly disintegrating tablet as mentioned in the present invention has enough practical hardness and can be rapidly dissolved in the buccal cavity.

INDUSTRIAL APPLICABILITY

According to the present invention, a tablet which can be rapidly disintegrated in oral cavity can be obtained.

What is claimed is:

1. A method of producing an intrabuccally rapidly disintegrating tablet, said intrabuccally rapidly disintegrating tablet comprising:
   a sugar alcohol or saccharide in the form of primary particles having an average particle size of not more than 30 µm;
   an active ingredient; and
   one or more disintegrants selected from the group consisting of crospovidone, croscarmellose sodium, low substituted hydroxypropylcellulose, and a mixture thereof, said method comprising the steps of:
   (a) granulating a powder material comprising the sugar alcohol or saccharide, thereby producing granulated material having a predetermined particle size;
   (b) mixing said granulated material with said active ingredient and said one or more disintegrants; and
   (c) compressing the mixture into an intrabuccally rapidly disintegrating tablet.

2. The method of claim 1, wherein the tablet disintegrates within 30 seconds as determined by measuring the time required for the tablet to fall through no. 10 wire mesh when water is added drop wise to the tablet at a rate of 4 mL/min.

3. The method of claim 1, wherein the amount of active ingredient ranges from 0.01-30% by weight of the intrabuccally rapidly disintegrating tablet.

4. The method of claim 1, wherein the sugar alcohol or saccharide is granulated to an average particle size of not more than 30 µm.

5. The method of claim 1, wherein the sugar alcohol or saccharide is selected from the group consisting of mannitol, lactose, and mixtures thereof.

6. The method of claim 1, wherein said method further comprises mixing the granulated material with a lubricant before said compressing step.

7. The method of claim 1, further comprising spraying a lubricant on one or more material contacting surfaces of punches and dies of a tabletting machine before said compressing step.

8. The method of claim 1, wherein said intrabuccally rapidly disintegrating tablet comprises about 60-95% by weight of said sugar alcohol or saccharide and about 1-10% by weight of said one or more disintegrants.

9. An intrabuccally rapidly disintegrating tablet made by the process of any of claims 1-8.

10. The method of claim 1, further comprising:
    (a1) drying the granulated material of step (a);
    (a2) mixing the dried granulated material of step (a1) with said active ingredient and said one or more disintegrants;
    (a3) spraying a lubricant on a material contacting surface of punches and dies of a tabletting machine before said compressing step (c); and
    wherein said compressing step (c) comprises compressing the mixture of step (a2).

11. The method of claim 10, wherein the granulating is wet granulating.

12. The method of claim 1, further comprising:
    (a1) drying the granulated material of step (a);
    (a2) blending the dried granulated material of step (a1) with one or more additional additives and/or lubricants to form a blend; and
    wherein said granulating step (a) is wet granulating, and said compressing of step (c) is compressing the blend of step (a2).

* * * * *